United States Patent [19]

Yamaguchi et al.

[11] Patent Number: 5,527,701

[45] Date of Patent: Jun. 18, 1996

[54] *ASPERGILLUS TERREUS* BLASTICIDIN S DEAMINASE, A BLASTICIDIN S DEAMINASE GENE, A VECTOR INCORPORATING SAID GENE AND A TRANSFORMANT CONTAINING SAID VECTOR

[75] Inventors: Isamu Yamaguchi; Makoto Kimura; Takashi Kamakura, all of Wakou, Japan

[73] Assignee: The Institute of Physical and Chemical Research, Japan

[21] Appl. No.: 53,006

[22] Filed: Apr. 27, 1993

[30] Foreign Application Priority Data

Aug. 25, 1992 [JP] Japan .................................. 4-226284

[51] Int. Cl.$^6$ .............................. C12N 5/14; C12N 15/55; C12N 15/63
[52] U.S. Cl. .................................. 435/240.4; 435/320.1; 536/23.2
[58] Field of Search .................................. 435/227, 240.2, 435/320.1, 252.3, 240.4; 536/23.2, 23.74

[56] References Cited

PUBLICATIONS

Yamaguchi et al., J. Antibiotics 28:7–14 (1975).
Yamaguchi et al., Agric. Biol. Chem. 49:3355–3361 (1985).
Kimura et al., Mol. Gen. Genet. 242:121–129 (1994).
Kobayashi et al., Agric. Biol. Chem. 55:3155–3157 (1991).
Kamakura et al., Agric. Biol. Chem. 51:3165–3168 (1987).
Yanai et al., Curr. Genet. 19:221–226 (1991).
Sutoh, Plasmid 30:150–154 (1993).

*Primary Examiner*—Robert A. Wax
*Assistant Examiner*—Eric Grimes
*Attorney, Agent, or Firm*—Finnegan, Henderson, Farabow, Garrett & Dunner

[57] ABSTRACT

According to the present invention, it is provided blasticidin S (hereinafter referred to as BcS) deaminase, a gene coding for the BcS deaminase, a vector incorporating the BcS deaminase gene and a transformant or a transductant transformed or transduced with the vector.

It is an object of the present invention to provide BcS deaminase, a BcS deaminase gene, a vector incorporating the BcS deaminase gene and a transformant containing the vector by focusing on the fact that blasticidin S is an aminonucleoside antibiotic capable of inhibiting a protein synthesis in the wide range of organisms and is generally used as an agricultural antibiotic.

It is another object of the present invention to establish expression vectors of above-mentioned BcS gene and to produce useful plants having drug resistance against specific agricultural chemicals.

4 Claims, 1 Drawing Sheet

5,527,701

ASPERGILLUS TERREUS BLASTICIDIN S DEAMINASE, A BLASTICIDIN S DEAMINASE GENE, A VECTOR INCORPORATING SAID GENE AND A TRANSFORMANT CONTAINING SAID VECTOR

INTRODUCTION

The present invention relates to a novel blasticidin S deaminase, a gene coding for said biasticidin S deaminase, a vector incorporating said gene and a transformant transformed with said expression vector.

BACKGROUND OF THE INVENTION

Recently, genetic manipulation has been frequently performed not only in animals but also in plants due to the development of biotechnology. When such genetic manipulation is performed, suitable vectors are usually chosen depending on types of host living organisms. In such vectors, markers are usually incorporated into host cells in order to know whether or not desired genes are incorporated into host cells. For example, a kanamycin resistance gene, a chloramphenicol resistance gene, and the like are used as representative markers.

However, it is necessary to pay a special attention in handling antibiotics corresponding to these drug-resistance markers from the viewpoint of medical and environment safety.

Therefore, it has been desired to establish vectors having relatively safe drug-resistance markers.

Furthermore, it is desired to attain more efficient agricultural production by producing useful plants having drug resistance against specific agricultural chemicals.

SUMMARY OF THE INVENTION

It is an object of the present invention to provide blasticidin S (hereinafter referred to as BcS) deaminase, a BcS deaminase gene, a vector incorporating the BcS deaminase gene and a transformant containing the vector by focusing on the fact that BcS is an antibiotic of the aminonucleoside family capable of inhibiting protein synthesis in the wide range of organisms and is generally used as an agricultural antibiotic.

It is another object of the present invention to establish expression vectors of above-mentioned BcS gene and to produce useful plants having drug resistance against specific agricultural chemicals.

According to the present invention, there are provided:
(1) BcS deaminase containing an amino acid sequence as described in SEQ ID No. 1
(2) A BcS deaminase gene coding for an amino acid sequence as described in SEQ ID No. 1
(3) A BcS deaminase gene comprising a base sequence as described in SEQ ID No. 2.
(4) A BcS deaminase gene comprising a base sequence as described in SEQ ID No. 3.
(5) A vector into which, as a bcS deaminase gene, a gene containing at least a base sequence as described in SEQ ID No. 2 is incorporated.
(6) A transformant or a transductant transformed or transduced with the vector described in (5).

DETAILED DESCRIPTION OF THE INVENTION

Figure 1:
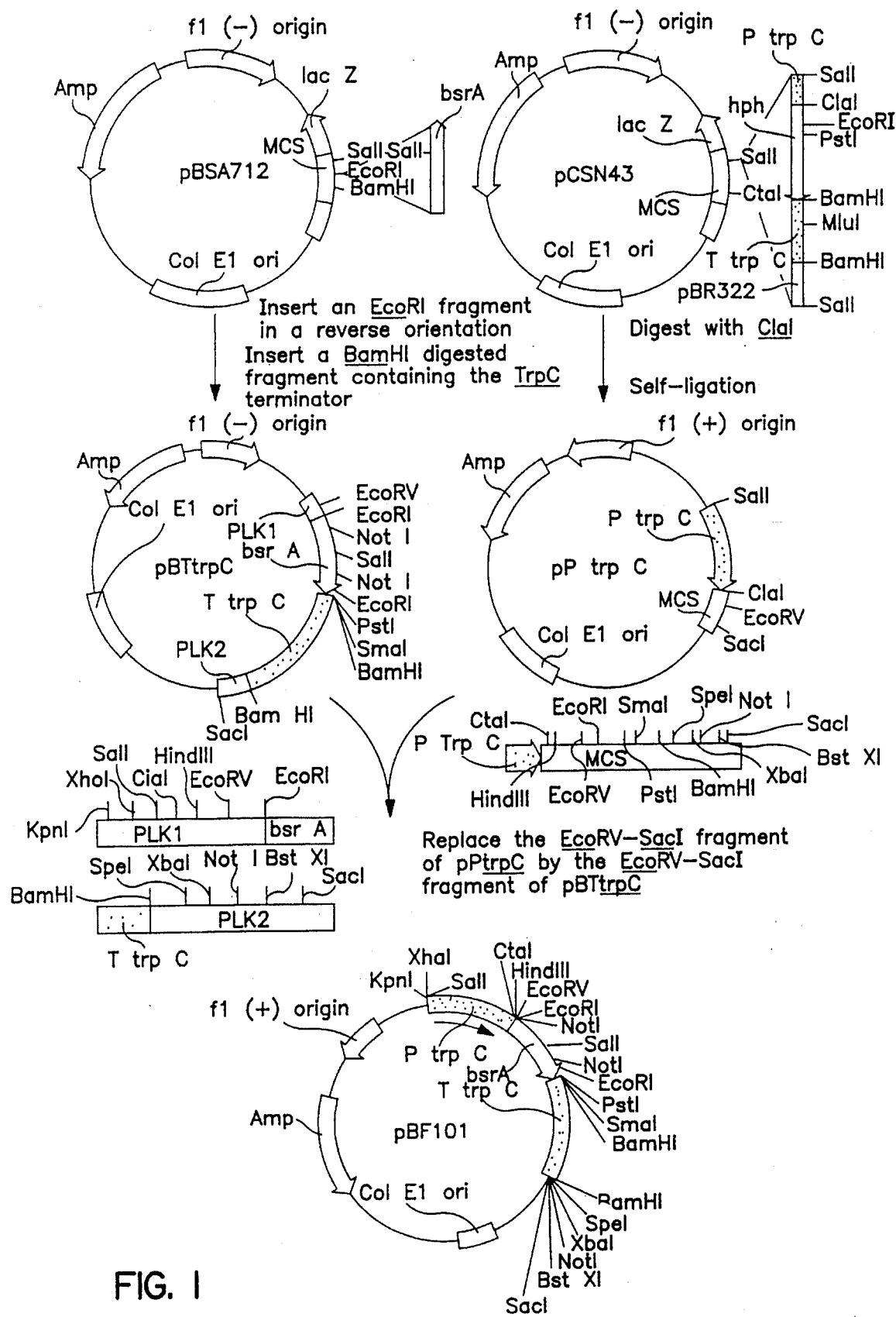
FIG. 1 shows a construction map of plasmid pBF101 comprising a vector into which the BcS deaminase gene of the present invention is incorporated.

Blasticidin S deaminase (hereinafter referred to as BcS deaminase) is an enzyme inactivating BcS and widely used as a major anti-rice-blast agent and the like these days.

The inventors previously isolated the gene bsr coding for a BcS deaminase from the plasmid of *Bacillus cereus* K55-S1, a BcS resistant strain (Kamakura et al., Agric. Biol. Chem., 51(11), 3165–3168(1987)), and introduced this bsr gene into the fungus *Pyricularia oryzae* that causes blast of rice. However, the BcS deaminase activity was not expressed. It should be noted that the blasticidin S deaminase (hereinafter referred to as BSD) gene of the present invention totally differs in the structure from the bsr described above.

A. Isolation of BSD

Isolation of BSD is performed by the conventional cloning method using cDNA of *Aspergillus terreus* S-712 (ATCC 28865), filamentous fungi known as a strain producing BcS deaminase.

mRNA is extracted from the mycelia of *Aspergillus terreus* S-712 cultured in the presence of BcS, and cDNA is synthesized using an oligo-dT primer. Then, the cDNA is incorporated into cloning vectors, which are introduced into hosts, thereby preparing a cDNA library. The transformant is replica-plated onto plates containing BcS, on which viable colonies are selected and proliferated, thereby isolating desired clones containing BSD.

Alternatively, when the base sequence of BSD is determined by the method described below, the above-mentioned cloning can be performed by the PCR method (Saiki et al., Science, 239, 487–491(1988)) using an oligonucleotide primer complementary to the base sequence of the BSD. In addition to the method described above, an immunological screening method, a hybrid molecule forming method, or the like can be used as screening methods.

B. The determination of the base sequence of BSD can be performed by Maxam-Gilbert chemical modification method (Maxam-Gilbert, Meth Enzym., 65, 499–560(1980)), Sanger method (F. Sanger et al., Proc. Natl. Acd. Sci. U. S. A., Vol. 74: pages 5463–5467(1977)), or the like. C. Then, a vector into which, as a BcS deaminase gene, a gene having at least a base sequence described in SEQ ID No. 2 is incorporated is constructed.

Starting vectors suitable for constructing the vector of the present invention can be chosen depending on types of hosts in which BSD is introduced.

For example, when *Escherichia coli* is used as a host, pBR322, pUC18, or the like can be used. When *Bacillus subtilis* is used, pHY300PLK ((Ishiwa et al., Jpn. J. Genet, 61, 515–528, (1986)) or the like can be used. When yeasts are used, pYEUra3 (Toyobo Co., Ltd.), pAU9 ((K. Okazaki et al., Nuc. Acids. Res., 18, 6485, (1990)), or the like can be used. When animal cells are used, pMAM-neo (F. Lee et al., Nature, 294, 228(1981)) or the like can be used. When plant cells are used, pBin19 (M. Bevan., Nuc., Acids. Res., 12, 8711(1984)), pLGV1103 (R. Hain et al., Mol Gen Genet, 199, 161(1985)) or the like can be used. In addition to the plasmid described above, a phage vector such as λZAPII, and a cosmid such as pWE15 (Stratagene) can be used.

In the construction of vectors, when vectors for procaryotes are employed as starting vectors, it is necessary to design vectors such that a promoter, a SD sequence, and the like are located upstream of a BSD structural gene. When vectors for eucaryotes are employed as starting vectors, it is necessary to design vectors such that vectors contain a promoter, an RNA splicing site, a polyadenylation site, and the like.

Furthermore, the expression of BSD is not restricted to direct expression of BSD. It is possible to express BSD as a part of a fusion protein by utilizing a base sequence coding for e.g., β-galactosidase, β-lactamase, or the like.

D. As a method for introducing the resulting vector into host cells and a method for transforming the host cell with the vector, customary methods can be used. For example, there may be employed a method, which comprises collecting cells in the exponential growth phase, and treating the collected cells with $CaCl_2$ in order to make them to be liable to incorporate a foreign DNA, thereby incorporating the above-mentioned vector into the $CaCl_2$-treated cells. In such a method, transduction can be carried out using $MgCl_2$ and $RbCl_1$ together in order to improve transformation efficiency.

The desired transformed strain thus obtained is cultured in accordance with conventional methods, thereby producing and accumulating BcS deaminase. Any one of various culture media conventionally used for a cell culture is available as a medium used in culture. For example, there may be L medium, E medium, M9 medium, and the like or media in which various kinds of known carbon sources, nitrogen sources, inorganic salts, vitamins and the like are added to the medium described above. Moreover, when the tryptophan promoter is used, it is preferred that cells be cultured in the above-mentioned medium (e.g. M9 minimum medium) containing casamino acid in order to enhance the promoter activity. Furthermore, an agent such as indoleacryl acid can be added to a medium at an appropriate time in the process of culturing to strengthen the tryptophan promoter activity.

The isolation and purification of BcS deaminase from the culture resulting from the above culturing can be carried out in accordance with conventional methods. In particular, when BcS deaminase is extracted from hosts, it is preferred to employ a mild extraction method, such as an osmosis-shock method, from a view point of maintaining a high-dimensional structure of BcS deaminase. The above-mentioned isolation and purification can be carried out in accordance with various treatment operations by utilizing physical properties or chemical properties of the polypeptide of BcS deaminase (see "Biochemical Data Book II", pp 1175–1259, the first edition, the first printing, published by Tokyo Kagaku Dojin on Jun. 23, 1980). As isolation and purification methods, for example, there may be employed a treatment using typical protein precipitation agents, or ultrafiltration, molecular-sieve chromatography (gel filtration), liquid chromatography, centrifugation, electrophoresis, affinity chromatography, dialysis, or the like. These method can be applied alone or in combination. The preferable embodiment for operations in the above methods are as follows:

BcS deaminase is partially purified from cultured cells. Partial purification is performed by a treatment using organic solvents such as acetone, methanol, ethanol, propanol, or demethylformamide (DMF); and salting-out agents such as ammonium sulfate, sodium sulfate, or sodium phosphate; and/or ultrafiltration using a dialysis membrane, a plate membrane, or a porous fibermembrane. For operation and conditions for each treatment, the same condition as those employed in the method described above can be generally employed. Then, the resulting crude product is subjected to gel filtration, thereby obtaining a fraction in which a BcS deaminase activity is detected. Agents used for gel filtration include, but are not limited to, materials, such as dextran-gel, polyacrylamide-gel, agarose-gel, polyacrylamide agarose-gel, cellulose, or the like. For example, there may be Sephadex G-type, Sephadex LH type, Sepharose type, Sephacryl type (all of these are from Pharmacia Fine Chemicals Co., Ltd.), Serofine (Chisso Corporation), Biogel P type, Biogel A type (Bio-Red Lab. Inc.) Ultrogel (LKB Co., Ltd), TSK-G type (Tosoh Corp.), or the like.

The BcS deaminase active fraction obtained by the above gel filtration is further purified, for example, by means of affinity chromatography, ion-exchange column chromatography (DEAE method), chromato-focusing, or a combination thereof, thereby isolating homogeneous BcS deaminase.

EXAMPLE

The present invention will be further described in more detail with reference to the following Examples.

Example 1 Isolation of BSD

*Aspergillus terreus* S-712 strain (ATCC 28865) was grown by stationary culture at 28° C. in a YG medium containing 250 µg/ml BcS. Then, the mycellia of the strain were separated from a culture solution using a spatula. Total RNA was extracted from the mycellia of the strain by the use of a Quick prep mRNA purification kit (Pharmacia K.K.) and mRNA was separated by means of a poly(dT) column. The first strand of DNA was synthesized with a reverse transcriptase (Pharmacia K.K.) using the mRNA as a template and an oligo(dT) as a primer. Subsequently, RNaseH, a DNA polymerase I, and dNTPs were added to the resultant solution, thereby synthesizing the second strand of DNA, that is, cDNA. The both ends of the cDNA were blunt-ended by a Klenow fragment, linked with an EcoRI-Not I adaptor (Pharmacia K.K.) using T4 DNA ligase and inserted into the EcoRI restriction site of *E. coli* phage vector λZAP II (Stratagene.).

The recombinant phage was packaged in vitro by the use of Gigapack II(Stratagene), infected into *E. coli* XL-1 Blue (Stratagene.) and harvested as λ phage particles. Then, 200 µl of *E. coli* XL-1 Blue (OD 600=1), 200 µl of a solution containing recombinant λ phage particles ($1 \times 10^5$) and 1 µl of filamentous helper phage R408 ($1 \times 10^6$ pfu/ml) (Stratagene) were combined and incubated at 37° C. for 15 minutes for double infection. After incubation, 5 ml of a 2X YT medium was added to the resultant culture solution. The mixture was further incubated at 37° C. for 3 hours, heated at 70° C. for 20 minutes, followed by centrifugation at 4000 × g for 5 minutes. The supernatant was collected. Recombinant filamentous phage particles were obtained which packaged a single-stranded DNA cleaved from *E. coli* phage vector λZAP II in vivo.

The phage particles were infected into *Escherichia coli* XL-1Blue, thereby obtaining *Escherichia coli* XL-1Blue containing cDNA as a phagemid. This *Escherichia coli* XL-1 Blue was replica-plated onto an LB-medium plate containing 150 µg/ml BcS, and colonies grown thereon were isolated. This isolation process was repeated 20 times. Of four colonies thus obtained, one colony was isolated as a clone containing BSD and designated as *Escherichia coli* XL-1Blue/pBSA712.

Composition of YG medium: 0.5% yeast extract and 2% glucose

Composition of 2X YT medium: 16% trypton, 10% yeast extract, and 5% NaCl,

Composition of LB medium: 10% trypton, 5% yeast extract, and 10% NaCl

Example 2 Construction of BcS Resistance Vector pBF101 Expressed in Filamentous Fungi.

The vector pCSN43 (Staben et al., Fungal Genet Newsl, 36, 79–81(1989)), which is designed such that hygromycin B resistance gene hph can be expressed by the promoter and the terminator of the TrpC gene derived from *Aspergillus nidulans* and is inserted in the unique Sal I site of pBS SK$^+$ (Stratagene), was digested with Cla I (TAKARA Co., Ltd.) at 37° C. for one hour. After digestion, a 2 kb fragment containing hph and the polyadenylation signal was removed. Then, the remaining digest was self-ligated with T4 DNA ligase, thereby obtaining vector pPtrpC having only the TrpC promoter upstream of a multi-cloning site(MCS).

Then, pBSA712 obtained in Example 1 was incubated with EcoRI (TAKARA Co., Ltd.) at 37° C. for one hour, followed by electrophoresis, thereby isolating a 559 bp fragment. The 559 bp fragment was inserted into the other half of the EcoRI digest such that a new construct contained the 559 fragment in a reverse orientation in relation to the original one. An approximately 700 bp fragment containing the TrpC terminator which had been obtained by the digestion of the above-described pCSN43 with Bam HI at 30° C. for one hour was inserted into the unique BamHI site downstream of the inserted 559 bp fragment, thereby obtaining pBTtrpC.

The pBTtrpC was digested with Sac I (TAKARA Co., Ltd.) and Eco RV (TAKARA Co., Ltd.) at 37° C. for one hour. The fragment between SacI site and EcoRV site of the above-mentioned pPtrpC was replaced for the 1,3 kb fragment containing the BSD gene and the polyadenylation signal, thereby obtaining BcS resistance vector pBF101 for filamentous fungi.

The pBF101 was introduced in *Escherichia coli* JM 109 which has been deposited with the National Institute of Bioscience and Human-Technology as *Escherichia coli* JM109/pBF101 under the accession No. FERM BP-4187.

A construction map of the above-described plasmid pBF101 is shown in FIG. 1.

Example 3 Transformation of *Escherichia coli* with pBSA712

*Escherichia coli* JM109 cultured overnight in an L medium described below was inoculated (1%v/v) in 10 ml of an L medium and cultured with shaking at 37° C. When a value of the turbidity (OD$_{550}$) reached 0.3 as measured by a turbidimeter, the cultured solution was centrifuged, and cells were collected and then suspended in 100 ml of a CaCl$_2$ solution. After the suspension was left standing overnight in an ice-cold condition, the plasmid DNA obtained in Example 1 was added to the suspension containing competent cells. The mixed solution was kept in an ice-cold condition for 30 minutes and heat-shocked at 37° C. for 30 minutes. In order to screen transformants using a BcS resistance marker, the heat-shocked suspension was immediately spread on an L-medium agar plate containing 150 µg/ml BcS and the plate was incubated at 37° C. As a result, BsC resistant colonies were appeared thereon, thereby obtaining transformed *Escherichia coli* JM109/pBSA712. The resulting transformant strain has been deposited with the National Institute of Bioscience and Human-Technology under the accession No. FERM BP-4186.

From this *Escherichia coli* JM109/pBSA712, was isolated plasmid DNA pBSA712 and the base sequence thereof was determined in accordance with the above-mentioned Sanger method. As a result, it was found that the plasmid DNA has a base sequence described in SEQ ID No. 3. It was presumed that the 393 bp sequence described in SEQ ID No. 2 within the 559 bp sequence is an open reading frame. It was also presumed that the open reading frame encodes an amino acid sequence described in SEQ ID No. 1.

Composition of L medium: 10% Bacto-trypton 5% yeast extract, 5%

NaCl, and 1% glucose (pH7.2)

Example 4 Isolation and purification of plasmids pBSA712 and pBF101

Cells of *Escherichia coli* strain JM109/pBSA712 incubated overnight in 5 ml of the above-mentioned L medium were collected by centrifugation and suspended in 200 µl of a buffer (pH 8.0) consisting of 20 mM Tris-HCl, 10 mM EDTA, and 50 mM glucose. To this mixture was added lysozyme to a final concentration of 10 mg/ml. The mixture was left standing at room temperature for 5 minutes, and 200 µl of 0.2N NaOH and a 1% SDS (sodium dodecyl sulfate) solution were added thereto. The mixture was gently mixed and left standing under ice-cold condition for 5 minutes. Then, 150 µl of 5M potassium acetate (pH 4.8) was added thereto, mixed well, left standing under ice-cold condition for 10 minutes, centrifuged and fractionated into a cell debris and a water-soluble fraction. To the resulting water-soluble fraction was added 600 µl of isopropyl alcohol and the solution was left standing at room temperature for 10 minutes to precipitate DNA. The resulting precipitate was collected and resuspended in 400 µl of a TE buffer containing 10 mM Tris-HCl and 1 mM EDTA. After protein was removed by phenol extraction, DNA was precipitated again with 2-volume of ethanol. The precipitate was resuspended in 150 µl of a TE buffer, treated with a ribonuclease to remove RNA. Then, 20% polyethylene glycol(6000) and 90 ml of a 2.5M NaCl solution were added thereto. As a result, only plasmid DNA was recovered as a precipitate (Yield; 5 µg).

To the recovered DNA was added distilled water, and 1/10 volume of 0.25% bromophenol blue and 5% glycerol were then added thereto.

The DNA solution thus obtained was subjected to agarose gel electrophoresis (0.8% agarose gel (60 mm ×4 mm)) using a buffer containing 40 mM Tris.HCl (4.8 mg Tris in 1 liter of distilled water), 2 mM EDTA.2 Na (0.74 g EDTA.2 Na in 1 liter of distilled water), and 0.14 ml of acetic acid (pH8.1), at an electric voltage of 100 V. As a result, it was confirmed that the plasmid DNA is a single plasmid.

*Escherichia coli* JM109/pBF101 was treated in the same manner as described above, thereby isolating a single pBF101.

Example 5 Extraction, Isolation and Purification of BcS deaminase

*Escherichia coli* JM109/pBSA712 strain obtained in Example 3 was incubated with shaking at 37° C. for 16 hours in 1 liter of an L medium, followed by centrifugation at 6000 × g for 6 minutes. The resulting cells were washed with 100 ml of a saline and, centrifuged at 6000 × g for 6 minutes twice. The cells were suspended in 5–10 ml of a 0.1M phosphate buffer (pH 7.2) containing 50% glycerine, disrupted by sonication, followed by centrifugation at 5000 × g for 6 minutes. To the supernatant (a crude enzyme solution) was added 20 % (w/v) $(NH_4)_2SO_4$. The reaction mixture was left standing at a temperature of 0°–4° C. for 30 minutes and centrifuged at 8500 × g for 20 minutes. To the supernatant was added $(NH_4)_2SO_4$ to a final concentration of 40% (w/v). The mixture was left standing at a temperature of 0°–4° C. for 30 minutes. To the resulting precipitation was added a 0.1M phosphate buffer containing 10% glycerine and 20 % (w/v) $(NH_4)_2SO_4$, in order to precipitate insoluble matter. A $(NH_4)_2SO_4$ solution was further added to precipitate enzyme until a concentration $(NH_4)_2SO_4$ reached to 40% (w/v).

The resultant enzyme was subjected to gel filtration using Sephadex G100 (an eluting solution containing a 0.01M Tris-HCl buffer (pH 7.5) and 2 mH DTT), thereby concentrating the enzyme. After the enzyme solution was dialyzed for 2 days, the concentrated enzyme was passed through an activated CH-Sepharose affinity column to which pyridimino blasticidin S was bounded as a ligand (an eluting solution: a 0.01M Tris-HCl buffer (pH 7.5)), thereby concentrating the BcS deaminase enzyme to be used as a sample.

Example 6 Confirmation of the Expression of BcS Deaminase

In order to confirm that the activity exhibited by *Escherichia coli* JM109/pBSA712 obtained in Example 3 was due to the expression of BcS deaminase, the enzyme activity was studied. The substrate BcS shows a maximum absorbance at a wavelength of 274 nm under an acidic condition. Deamino-BcS, the product of an enzyme-substrate reaction, shows a maximum absorbance at a wavelength of 258 nm. Therefore, a BcS-resistant and a BcS-sensitive strain were respectively incubated with a buffer containing BcS. UV spectra of the respective supernatants of the reaction mixtures were measured under an acidic condition, thereby detecting the enzyme activity in terms of a shift of the absorbance. A BcS solution in which parental strain Escherichia Coli JM109 was incubated at 30° C. for one hour kept showing an absorbance at 274 nm. On the contrary, a BcS solution in which *Escherichia coli* JM109/pBSA712 was incubated showed an absorbance shift to 258 nm. As a result, the presence of a BcS deaminase activity was demonstrated in the solution containing *Escherichia coli* JM109/pBSA712.

Example 7 Transformation of Filamentous Fungi with pBF101

A section (3 disks) containing the fungus *Pyricuraria oryzae* P2 that causes blast of rice was punched out from a plate using a cork borer and cultured in 100 ml of a YG liquid medium with shaking at 28° C. for 2 days. 5 ml of the culture was inoculated in 100 ml of a fresh YG liquid medium and cultured overnight, followed by centrifugation. The cells thus obtained were washed with sterilized water twice, and with an OM buffer twice and treated with an enzyme solution containing Novozyme 234 at 28° C. for 2 hours, thereby obtaining protoplasts. To the resulting protoplast solution was gently layered 0.5 volume of a ST buffer, followed by centrifugation at 4000 × g for 10 minutes, thereby collecting the protoplast at the interface. The protoplast was washed with 2-volume of a STC buffer and then suspended in a STC buffer so as to have a concentration of 108–109/ml. To 100 μl of the protoplast solution was added 5 μl of a DNA solution (0.5 μg/l). The mixture was gently stirred and allowed to stand still at room temperature for 25 minutes. To the mixture were added 200 μl, 200 μl and 800 μl of PEG solution (1,200 μl in total) in that order and incubated at room temperature for 20 minutes and subjected to centrifugation at 1000 × g for 5 minutes. The supernatant containing PEG was discarded and the residue was incubated with shaking in 2.5 ml of a YSG liquid medium for 2 hours. Cells were collected again, resuspended in an STC solution, and spread onto an agar-medium containing 20 μg/ml BcS. About 5 ml of 1% Sea Plaque (low melting agarose containing 1.2 M sorbitol, from FMC Co., Ltd.) containing 20 μg/ml BcS was layered on the spread. After solidification, the plate was covered with a parafilm, and incubated at 28° C. Transformants appeared about 5 days later. The transformation efficiency was approximately 200 colonies/μg DNA.

YG medium: 0.5% yeast extract, and 2 % glucose

OM buffer: 1.2M $MgSO_4$, and 10 mM sodium phosphate (pH5.8)

Novozyme 234 enzyme solution: 5 mg/ml Novozyme 234 in an OM buffer

ST buffer: 0.6M sorbitol, and 100 mM Tris-HCl (pH 7.5)

STC buffer: 0.2M sorbitol, 100 mM Tris-HCl (pH 7.5), and 20 mM $CaCl_2$

PEG solution: 60% PEG 4000, 10 mM $CaCl_2$, and 10 mM Tris-HCl (pH 8.0)

YGS medium: 0.5% yeast extract, 2% glucose, and 1.2M sorbitol

---

What is claimed is:

1. A blasticidin S deaminase gene comprising the base sequence of SEQ ID No. 2.

2. A blasticidin S deaminase gene comprising the base sequence of SEQ ID No. 3.

3. A vector into which, as a blasticidin S deaminase gene, a gene containing at least the base sequence of SEQ ID No. 2 is incorporated.

4. A plant cell transformed or transduced with the vector according to claim 3.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 130 amino acids
        ( B ) TYPE: amino acid
        ( D ) TOPOLOGY: unknown (i i) MOLECULE TYPE: other
    (A) DESCRIPTION: polypeptide (v i) ORIGINAL SOURCE:
    (A) ORGANISM: Aspergillus Terreus S-712 (ATCC 28865)

(x i) SEQUENCE DESCRIPTION: SEQ ID NO:1:

| Met | Pro | Leu | Ser | Gln | Glu | Glu | Ser | Thr | Leu | Ile | Glu | Arg | Ala | Thr | Ala |
|-----|-----|-----|-----|-----|-----|-----|-----|-----|-----|-----|-----|-----|-----|-----|-----|
| 1 | | | | 5 | | | | | 10 | | | | | 15 | |
| Thr | Ile | Asn | Ser | Ile | Pro | Ile | Ser | Glu | Asp | Tyr | Ser | Val | Ala | Ser | Ala |
| | | | 20 | | | | | 25 | | | | | 30 | | |
| Ala | Leu | Ser | Ser | Asp | Gly | Arg | Ile | Phe | Thr | Gly | Val | Asn | Val | Tyr | His |
| | | 35 | | | | | 40 | | | | | 45 | | | |
| Phe | Thr | Gly | Gly | Pro | Cys | Ala | Glu | Leu | Val | Val | Leu | Gly | Thr | Ala | Ala |
| | 50 | | | | | 55 | | | | | 60 | | | | |
| Ala | Ala | Ala | Ala | Gly | Asn | Leu | Thr | Cys | Ile | Val | Ala | Ile | Gly | Asn | Glu |
| 65 | | | | | 70 | | | | 75 | | | | | | 80 |
| Asn | Arg | Gly | Ile | Leu | Ser | Pro | Cys | Gly | Arg | Cys | Arg | Gln | Val | Leu | Leu |
| | | | | 85 | | | | | 90 | | | | | 95 | |
| Asp | Leu | His | Pro | Gly | Ile | Lys | Ala | Ile | Val | Lys | Asp | Ser | Asp | Gly | Gln |
| | | | 100 | | | | | 105 | | | | | 110 | | |
| Pro | Thr | Ala | Val | Gly | Ile | Arg | Glu | Leu | Leu | Pro | Ser | Gly | Tyr | Val | Trp |
| | | 115 | | | | | 120 | | | | | 125 | | | |
| Glu | Gly | | | | | | | | | | | | | | |
| | 130 | | | | | | | | | | | | | | |

(2) INFORMATION FOR SEQ ID NO:2:

(i) SEQUENCE CHARACTERISTICS:
        (A) LENGTH: 393 base pairs
        (B) TYPE: nucleic acid
        (C) STRANDEDNESS: double
        (D) TOPOLOGY: linear (i i) MOLECULE TYPE: cDNA to mRNA (v i) ORIGINAL SOURCE:
        (A) ORGANISM: Aspergillus Terreus S-712 (ATCC 28865)

(x i) SEQUENCE DESCRIPTION: SEQ ID NO:2:

```
ATGCCTTTGT CTCAAGAAGA ATCCACCCTC ATTGAAAGAG CAACGGCTAC AATCAACAGC      60
ATCCCCATCT CTGAAGACTA CAGCGTCGCC AGCGCAGCTC TCTCTAGCGA CGGCCGCATC     120
TTCACTGGTG TCAATGTATA TCATTTTACT GGGGGACCTT GTGCAGAACT CGTGGTGCTG     180
GGCACTGCTG CTGCTGCGGC AGCTGGCAAC CTGACTTGTA TCGTCGCGAT CGGAAATGAG     240
AACAGGGGCA TCTTGAGCCC CTGCGGACGG TGTCGACAGG TGCTTCTCGA TCTGCATCCT     300
GGGATCAAAG CGATAGTGAA GGACAGTGAT GGACAGCCGA CGGCAGTTGG GATTCGTGAA     360
TTGCTGCCCT CTGGTTATGT GTGGGAGGGC TAA                                  393
```

(2) INFORMATION FOR SEQ ID NO:3:

(i) SEQUENCE CHARACTERISTICS:
        (A) LENGTH: 559 base pairs
        (B) TYPE: nucleic acid
        (C) STRANDEDNESS: double
        (D) TOPOLOGY: linear (i i) MOLECULE TYPE: cDNA to mRNA (v i) ORIGINAL SOURCE:
        (A) ORGANISM: Aspergillus Terreus S-712 (ATCC 28865)

(x i) SEQUENCE DESCRIPTION: SEQ ID NO:3:

```
                 GAATTCGCG  GCCGCCACAA  TTGCCCACCA  TCAGCCATCT  CATTGTCAAT    -49
ATGCCTTTGT  CTCAAGAAGA  ATCCACCCTC  ATTGAAAGAG  CAACGGCTAC  AATCAACAGC     60
ATCCCCATCT  CTGAAGACTA  CAGCGTCGCC  AGCGCAGCTC  TCTCTAGCGA  CGGCCGCATC    120
TTCACTGGTG  TCAATGTATA  TCATTTTACT  GGGGGACCTT  GTGCAGAACT  CGTGGTGCTG    180
GGCACTGCTG  CTGCTGCGGC  AGCTGGCAAC  CTGACTTGTA  TCGTCGCGAT  CGGAAATGAG    240
AACAGGGGCA  TCTTGAGCCC  CTGCGGACGG  TGTCGACAGG  TGCTTCTCGA  TCTGCATCCT    300
GGGATCAAAG  CGATAGTGAA  GGACAGTGAT  GGACAGCCGA  CGGCAGTTGG  GATTCGTGAA    360
TTGCTGCCCT  CTGGTTATGT  GTGGGAGGGC  TAAGCACCAG  CCATTGATCT  TGTACATTCA    420
AGCTACTTTC  TGTTACTAGA  TGAACCGAGC  ATGAGTTGAT  GGTGAATGCA  TACAGAGTAC    480
AATGGTGGAA  AAAAAAGCGG  CCGCGAATTC                                        510
```